United States Patent [19]

Bonderman

[11] 4,011,045
[45] Mar. 8, 1977

[54] TURBIDITY REDUCTION IN TRIGLYCERIDE STANDARDS

[76] Inventor: Dean P. Bonderman, 586 W. 77th North Drive, Indianapolis, Ind. 46260

[22] Filed: Feb. 14, 1975

[21] Appl. No.: 549,940

[52] U.S. Cl. .............................. 23/230 B; 195/3 R; 195/103.5 R; 252/408

[51] Int. Cl.[2] ................. G01N 31/02; G01N 31/14

[58] Field of Search ............. 23/230 B; 260/112 B; 252/408

[56] References Cited

UNITED STATES PATENTS

| | | | |
|---|---|---|---|
| 3,260,648 | 7/1966 | Fox | 23/230 B |
| 3,274,062 | 9/1966 | Lou | 252/408 |
| 3,682,835 | 8/1972 | Louderback | 23/230 B X |
| 3,703,591 | 11/1972 | Bucolo et al. | 195/103.5 R |
| 3,751,381 | 8/1973 | Megraw | 23/230 B X |
| 3,869,349 | 3/1975 | Goodhue | 195/103.5 R |
| 3,893,990 | 7/1975 | Fekete | 260/112 B |
| 3,898,130 | 8/1975 | Komatsu | 195/103.5 R |
| 3,901,655 | 8/1975 | Shukla et al. | 23/230 B |

*Primary Examiner*—Barry S. Richman
*Assistant Examiner*—Michael S. Marcus
*Attorney, Agent, or Firm*—Woodard, Weikart, Emhardt & Naughton

[57] ABSTRACT

Methods and preparations which function to reduce the turbidity normally associated with triglyceride standards. A method is disclosed of preparing serum suitable for use as a triglyceride standard in which the triglyceride level normally present in the serum is reduced and glycerides of fatty acids having from 5 to 10 carbon atoms are added to the serum. A suitable surfactant for emulsifying the triglycerides is added, the surfactant being an alkylphenoxypolyethoxyethanol having 6 to 10 ethoxy groups. The serum is then lyophilized or frozen and upon reconstitution or thawing, virtually no turbidity exists.

17 Claims, No Drawings

TURBIDITY REDUCTION IN TRIGLYCERIDE STANDARDS

BACKGROUND OF THE INVENTION

1. Field of the Invention

The invention relates to standards used in assaying for triglyceride levels.

2. Description of the Prior Art

The prior art is believed best set forth in U.S. Pat. No. 3,853,465, which is hereby incorporated by reference. Generally this patent sets forth the facts of difficulties in photometric analysis which result from turbidity in serum and plasma samples. This is due primarily to triglycerides present in the serum. The solution to this turbidity problem which U.S. Pat. No. 3,853,465 sets forth is to add a surfactant to the serum or plasma to reduce the turbidity. This patent discloses a surfactant of polyoxyethylated lauric acid having from 9 to 20 ethoxy groups. Compounds of this general class which have from 10 to about 20 ethoxy groups are disclosed in U.S. Pat. No. 3,260,648 for use as an emulsifier for cholesterol in serum. This latter patent sets forth the use of a lower alkylphenoxypolyethoxyethanol having from about 10 to about 20 ethoxy groups. While the use of such surfactants does result in an improvement in turbidity in serum, the products produced tend to be metastable and separate after a period of time. Additionally, large amounts of surfactant are generally required and such large amounts of surfactant interfere with biological assays of serum ingredients. Moreover, even with the surfactants of this type, reconstitution of lyophilized serum having elevated triglyceride levels produces measurable turbidity notwithstanding the use of the surfactants.

In addition to the above-mentioned patents, a triglyceride standard is disclosed in an article by Chong-Kit and McLaughlin published in Clinical Chemistry, Volume 20, No. 11 (1974). This standard uses triolein emulsified with isooctylphenoxypolyethoxyethanol having an average of 9 to 10 ethylene oxide groups. This standard is prepared by heating to elevated temperatures and mixing triolein with the surfactant. This mixture is also metastable and tends to become cloudy with time. More importantly, it cannot be frozen or lyophilized and then reconstituted or thawed without producing a cloudy solution. Even more importantly, the temperatures set forth for manufacturing the standard are too high to permit the procedure to be used with serum without risking destruction of enzymes desired in the serum.

SUMMARY OF THE INVENTION

The invention is particularly pointed out in the claims, and reference should be made thereto to determine the scope of the invention. Generally, however, one aspect of the invention can be said to relate to the replacing of triglycerides normally present in serum with glycerides of fatty acids having from 5 to 10 carbon atoms. This enables the serum to be subsequently lyophilized or frozen and thereafter be reconstituted or thawed without any turbidity. A surfactant is used to assist in the suppression of turbidity after reconstitution or thawing. This surfactant is an alkylphenoxypolyethoxyethanol containing an average of from 6 to 10 ethoxy groups and in which the alkyl group contains from about 5 to about 14 carbon atoms. Another aspect of the invention is a technique for reducing the triglyceride level normally present in serum which is accomplished by adding lipase to the serum for a sufficiently long time to reduce the triglyceride level to below about 0.02% of the serum and then lyophilizing the serum.

DETAILED DESCRIPTION OF THE INVENTION

The invention relates to a method of preparing serum which is suitable for use as a triglyceride standard and which has three basic steps. The first step is the reduction of the triglyceride level normally present in the serum. The second step is to add glycerides of fatty acids having from 5 to 10 carbon atoms to achieve a concentration of at least 0.03% of the amount of the serum and adding an effective amount of an alkylphenoxypolyethoxyethanol surfactant to solubilize the glycerides. The surfactant should contain an average of from 6 to 10 ethoxy groups and the alkyl group of the surfactant should contain about 5 to about 14 carbon atoms. The third step in the method is to preserve the serum by lyophilizing or freezing. Then when it is desired to use the serum, the serum can be reconstituted or thawed without adverse effects on the clarity of the serum.

As to step 1, the reduction of the triglyceride level can be accomplished in many ways. They can be reduced by ethanol fractionation extraction with a solvent from lyophilized serum, by precipitation of lipoprotein with dextran sulfate or another similar polysulfate or by the addition of lipase with or without the subsequent removal of free fatty acids. The use of lipase or precipitation with a polysulfate are preferred, depending upon the quality of serum desired.

Reduction of the triglyceride level with lipase is easily accomplished by the addition of lipase either in purified form or as pancreatin. The enzyme is then allowed to break down the triglycerides present in the serum. After the triglyceride level has been reduced, preferably to below 0.02% of the serum, the lipase will either have lost activity because of its inherent property of being a labile enzyme which is subject to autodegradation or if the lipase has not lowered to a sufficiently low level of activity, it can be reduced in activity by heating for a short period of time, preferably at about 50° C. for about 10 minutes. It should be pointed out that the serum standard produced by the action of lipase, whether or not the lipase activity is eventually reduced, provides a much better serum standard for tests other than triglyceride because it can be lyophilized and reconstituted (or frozen and thawed) without any resultant turbidity. This technique of reducing triglycerides is very specific to the triglycerides and does not interfere with other constituents of the serum. If the serum is to be made into a triglyceride standard, then it is desirable to reduce the lipase activity to below 0.5 units before adding the glyceride of step 2. Careful choice of the quantity of lipase added and the time of action of the lipase can eliminate any need for elevated temperatures to accelerate the degradation of the lipase.

After the lipase has been added to the serum, it may be desirable to remove the free fatty acids which are formed from the action of lipase. If this is the case, they may be removed by passage through an ion exchange resin such as a mixed bed resin.

As an alternative to the lipase technique for reducing the triglyceride level, one can precipitate the lipoproteins which contain the triglycerides and remove the precipitate to reduce the lipoprotein concentration. The basic technique for removing triglyceride containing lipoproteins is set forth in patent application Ser. No. 414,799 filed by Proksch and Bonderman. The technique of precipitating triglyceride containing lipoproteins is disclosed by Burstein, Scholnick, and Morfin in the *Journal of Lipid Research*, Volume II (1970), Pages 583 to 595.

Basically, this precipitation method incorporates the steps of adding to the serum a metal cation selected from the group consisting of calcium, manganese and magnesium, adding to this, a quantity of a polysulfate sufficient to precipitate a triglyceride-containing-lipoprotein-polysulfate complex, the polysulfate being a polymer having a molecular weight of at least 10,000 and having at least one sulfate group per monomer. A precipitate then forms which is removed and the excess metal cations may be removed either by precipitation or dialysis or any other suitable technique.

The second step of the procedure relates to the addition, to the serum which has had its triglyceride level reduced, of glycerides of fatty acids having from 5 to 10 carbon atoms to achieve a concentration of at least 0.03%. More preferably, glycerides or fatty acids having from 8 to 10 carbon atoms are added because glycerides of fatty acids having from 5 to 7 carbon atoms do not measure accurately in most assay or analysis procedures. The preferred additive is tricaprylin This measures accurately in all procedures and provides maximum clarity in the final product. The use of only triolein is inappropriate with this invention as it will not produce a clear solution after reconstitution of a lyophilized product. The use of glycerides of fatty acids of less than 5 carbon atoms is not appropriate since not only do they not measure quantitatively in all procedures, they volatilize when lyophilized and therefore are inappropriate for producing a lyophilized serum.

A surfactant is also added to aid in the dissolution of the glycerides which are added. This surfactant which is added is an alkylphenoxypolyethoxyethanol. An effective amount of this surfactant is used, and generally less than 0.05% is needed. The surfactant should contain an average of from six to 10 ethoxy groups and from about 5 to about 14 carbon atoms in the alkyl group. This provides the appropriate water solubility and pincer effect for solubilizing the glycerides. Preferably, the alkylphenoxy group is either o-nonylphenoxy or o-octylphenoxy. The two surfactants which have been found to work best are Triton X-114 and Triton N-101 made by Rohm & Haas. Chemically these are respectively octylphenoxy poly(7-8)ethoxyethanol and nonylphenoxy poly (9-10)ethoxyethanol.

The third step is the lyophilization or freezing of the modified serum. Lyophilization is preferred. It is also preferred that the preparation prior to lyophilization or freezing not have over 0.02% of glycerides of greater than C12 fatty acids.

In addition to a serum standard, a non-serum triglyceride standard could equally well be made by addition of the glycerides of from C5 to C10 fatty acids, preferably of from C8 to C10 fatty acids to water and the addition thereto of the surfactants referred to above. This standard can be made up having at least 0.03% of the glycerides or in concentrated form for adding as a diluent which would contain at least 1% of the glycerides.

EXAMPLE I

A normal 2000 ml. pooled human blood plasma sample was obtained, and calcium chloride was added to achieve a 0.06 molar concentration of calcium cation in the plasma. The pH was adjusted to 7.4 using 3.0 ml. of 6N NaOH. The mixture was then heated to 37° C. and 2 ml. of topical bovine thrombin (100 NIH units per ml.) was added. The plasma was allowed to clot and the serum was then expressed from the clot. Dextran sulfate was added to the serum to achieve a concentration of 5 g/l. A flocculant lipoprotein-complex precipitate was formed at pH 7.4. The precipitate was subsequently removed and discarded.

A concentrate was then prepared and added in the amount of 10 ml. to the serum base previously prepared. The concentrate is prepared by mixing 5.0 grams of tricaprylin (trioctanoin), (Sigma T9126) and 25 ml. of Triton X-114. This mixture was swirled and heated at 60° C. for 15 minutes, cooled to room temperature and diluted with distilled water to 100 ml. 10 ml. of this concentrate is then added to 990 ml. of the serum. This resulted in only 2.5 ml. of surfactant in 1000 ml. of serum. The material was then lyophilized and reconstituted. The reconstituted serum had no interference in any parameter measured and had no turbidity. Similar results were achieved by freezing the serum and thawing it prior to use. Solubilization of the lyophilized material was enhanced due to the small amount of surfactant.

The triglyceride level was 97.5 mg. per dl.

Additional tests were run increasing the amount of concentrate added so as to achieve triglyceride levels in the serum of 200, 400, 500 and 700 mg. per dl. Levels above 500 mg. per dl. result in some degree of interference with the lyophilization process but otherwise were satisfactory.

EXAMPLE II

A concentrate was prepared as set forth in Example I and was used as a diluent in addition to water to reconstitute lyophilized serum from which the triglyceride had been removed. The resultant serum measured quantitatively both in analytical procedures which extract triglyceride with a solvent as well as with enzymatic tests.

EXAMPLE III

A concentrate prepared as set forth in Example I was diluted with distilled water to achieve a 0.1% concentration of triglyceride and used as a triglyceride standard. Excellent results were achieved with essentially perfect optical clarity.

EXAMPLE IV

Heparinized plasma was assayed for factor V activity. Since activity was not present, 100 ml. of fresh plasma containing factor V (proaccelerin) was added to each liter of material. The material was warmed to 37° C., and brought to pH 7.4 with concentrated NaOH and then 1 gm. of Celite containing 1 millimole of $CaCl_2$ was added. While stirring, 0.1 gm. of pancreatin (Sigma P1750) was added. After a clot was formed, the material was allowed to set at 10° C. for 24 hours. The clot was removed and the material was assayed for a lipase (0.3 units) and triglyceride level (0.01%) by the methods of Cherry-Crandall and Levy-Kaloun, respectively. Since the triglyceride content was less than 0.03% and the lipase activity had diminished to less than 0.5 units, the material was clarified by centrifugation to remove crude precipitates. Before dispensing, the concentrate as prepared in Example I was added. After mixing, the serum was dispensed and lyophilized.

In the event that triglyceride level is too high and lipase activity is low, additional pancreatin (i.e. 50 mg. per liter) can be added and the serum allowed to stand until the triglyceride level is reduced to an acceptable level. If the triglyceride level is low and the lipase level is high, the serum can be incubated at 50° C. for 10 minutes with stirring to accelerate the auto-degradation and heat degradation of the lipase.

After reconstitution, the serum was optically clear and triglyceride measured accurately with extraction and enzymatic tests. No interference with other assays was noted.

EXAMPLE V

Variations of Example IV were tried substituting equivalent amounts of glycerol dicaprylate, glycerol monocaprate, tricaprin and tricaproin and by using a purified form of lipase in place of pancreatin. Similar results were achieved except that with tricaprin, results were about 50% low in extraction measuring tests.

EXAMPLE VI

The serum of Example IV was prepared but without addition of concentrate. After lyophilization and reconstitution, the serum was very clear and was suitable for use as a serum standard for all normal constituents except triglycerides.

Unless otherwise stated, percentages set forth herein are by weight. The term serum used in the claims is to be interpreted broadly to encompass plasma. The scope of the invention is to be determined the following claims and equivalents thereof.

EXAMPLE VII

The preceding examples were performed using Triton N-101 in place of Triton X-114. Identical results were obtained.

EXAMPLE VIII

The serum of Example IV was additionally treated prior to lyophilization by passage through a mixed bed resin. This procedure removed a large portion of the free fatty acids produced by the action of the lipase in the pancreatin.

What is claimed is:
1. A method of preparing serum which is suitable for use as a triglyceride standard comprising:
   a. reducing the triglyceride level normally present in the serum,
   b. after said reducing, adding to the serum glycerides of fatty acids having from 5 to 10 carbon atoms to achieve a concentration of at least 0.03% and an effective amount of an alkyl-phenoxy polyethoxyethanol surfactant for solubilizing said added glycerides, said surfactant containing an average of from 6 to 10 ethoxy groups, and the alkyl group of said surfactant containing from about 5 to about 14 carbon atoms, and
   c. preserving the serum by lyophilizing or freezing the serum to which said added glyceride has been added.

2. A method of preparing a lyophilized form of the serum of claim 1 in which said preserving is accomplished by lyophilizing.
3. The method of claim 1 in which said reducing is accomplished by adding lipase to the serum and allowing the lipase to reduce the triglyceride level.
4. The method of claim 3 in which the triglyceride level is reduced to below 0.02% of the serum before said adding of a glyceride.
5. The method of claim 3 in which the lipase activity is reduced to below 0.5 units before said adding of a glyceride.
6. The method of claim 5 in which the reduction of lipase activity is accomplished by heating at about 50° C for about 10 minutes.
7. The method of claim 1 in which said alkyl-phenoxy group is selected from the group consisting of o-nonyl phenoxy and o-octyl phenoxy.
8. The method of claim 1 in which said added glyceride is a triglyceride.
9. The method of claim 8 in which said triglyceride is tricaprylin.
10. The method of claim 9 in which said alkyl group in nonyl or octyl.
11. The method of claim 1 in which said reducing is accomplished by precipitating triglyceride-containing lipoproteins by:
    a. adding to the serum a metal cation selected from the group consisting of: calcium, manganese and magnesium;
    b. adding to the serum containing the added metal cation a quantity of polysulfate sufficient to precipitate a triglyceride-containing-lipoprotein-polysulfate complex, said polysulfate being a polymer having a molecular weight of at least 10,000 and having at least one sulfate group per monomer; and
    c. removing the precipitate which forms.
12. The method of claim 11 in which said glyceride is tricaprylin.
13. The method of claim 1 in which at least 0.1% of the glyceride of a fatty acid having from 5 to 10 carbon atoms is added to the serum.
14. The method of claim 1 in which the glyceride is of a fatty acid having from 8 to 10 carbon atoms.
15. The method of claim 14 in which the glyceride is tricaprylin.
16. A method of preparing serum which is suitable for use as a triglyceride standard comprising:
    a. reducing the triglyceride level normally present in the serum,
    b. preserving the serum by lyophilizing or freezing the serum to which said added glyceride has been added.
    c. after said preserving, adding to the serum a liquid preparation comprising the combination of an aqueous solution of glycerides of from C5 to C10 fatty acids, said glycerides being present at a concentration of at least 0.03% of the solution, and an alkyl-phenoxy polyethoxyethanol surfactant suitable for solubilizing said glycerides said surfactant being present in an amount effective to solubilize said glycerides and in which the polyethoxyethanol group contains an average of from 6 to 10 ethoxy groups and the alkyl group contains from about 5 to about 14 carbon atoms.
17. The method of claim 16 in which said liquid preparation contains said glyceride at a concentration of at least 1% of the liquid preparation.

* * * * *